United States Patent
Westbye et al.

(10) Patent No.: US 7,294,119 B2
(45) Date of Patent: Nov. 13, 2007

(54) PASSIVE DELIVERY SYSTEM DILUENTS MIXING AND DELIVERY

(75) Inventors: Lars Tommy Westbye, Carlsbad, CA (US); Philip Dowds, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 525 days.

(21) Appl. No.: 10/866,434

(22) Filed: Jun. 10, 2004

(65) Prior Publication Data

US 2005/0277894 A1    Dec. 15, 2005

(51) Int. Cl.
*A61M 5/00*    (2006.01)
(52) U.S. Cl. .......................................... 604/187; 604/82
(58) Field of Classification Search ................ 604/187, 604/82–92, 411, 414
See application file for complete search history.

(56) References Cited

U.S. PATENT DOCUMENTS

| | | | |
|---|---|---|---|
| 3,548,824 A | | 12/1970 | Carr |
| 4,060,082 A | | 11/1977 | Lindberg et al. |
| 5,320,603 A | | 6/1994 | Vetter et al. |
| 5,569,193 A | | 10/1996 | Hofstetter et al. |
| 5,779,668 A | | 7/1998 | Grabenkort |
| 5,785,682 A | * | 7/1998 | Grabenkort ................. 604/82 |
| 5,971,953 A | | 10/1999 | Bachynsky et al. |
| 6,186,980 B1 | | 2/2001 | Brunel |
| 6,364,865 B1 | | 4/2002 | Lavi et al. |
| 6,440,101 B1 | | 8/2002 | Grabenkort et al. |

(Continued)

FOREIGN PATENT DOCUMENTS

| | | |
|---|---|---|
| GB | 2079607 A | 1/1982 |
| WO | WO 95/31235 A | 11/1995 |

(Continued)

OTHER PUBLICATIONS

Instructions for Use for Bio-Set Injection from Bio-Set Website, printed Jan. 14, 2003 (http://www.bio-set.com/htm/InstUseInj.htm).

(Continued)

*Primary Examiner*—Kevin C. Sirmons
*Assistant Examiner*—Catherine N. Witczak
(74) *Attorney, Agent, or Firm*—Orrick, Herrington & Sutcliffe LLP

(57) ABSTRACT

A syringe system for the administration of lyophilized drugs includes a syringe barrel and a stopper and a needled guard each coupled with the syringe barrel. A reconstitution plunger is removably coupled with the stopper. A diluent is withdrawn from the syringe into a vial containing a lyophilized drug, and the diluent and drug are mixed to form a therapeutic agent. The reconstitution plunger is then replaced by an administration plunger. The length of the reconstitution plunger is greater than the length of the administration plunger in order to prevent activation of the needle guard during reconstitution. Alternatively, a single plunger system may be used in which the plunger can transition from an extended length during reconstitution to a shortened length during administration. During administration, a radial element of the plunger contacts latch members of the needle guard, whereupon the shield advances to an extended position covering the needle.

19 Claims, 8 Drawing Sheets

U.S. PATENT DOCUMENTS

| | | |
|---|---|---|
| 6,474,369 B2 | 11/2002 | Castellano |
| 6,478,771 B1 | 11/2002 | Lavi et al. |
| 6,623,459 B1 * | 9/2003 | Doyle .................. 604/197 |

FOREIGN PATENT DOCUMENTS

| | | |
|---|---|---|
| WO | WO 01/45776 A | 6/2001 |
| WO | WO 02/072182 A | 9/2002 |
| WO | WO 02/076542 A | 10/2002 |

OTHER PUBLICATIONS

Press Release from PRWeb Website entitled "Second Patent For Mixing Lyophilized (Freeze-Dried) Drugs In A Needle-Less Injector Awarded To Penject® Corporation," printed Jan. 14, 2003 (http://www.prweb.com/printer.php?prid=31822).

* cited by examiner

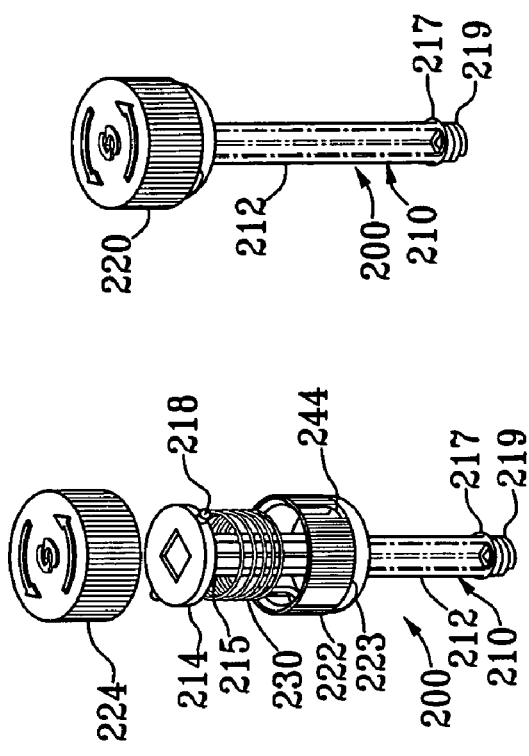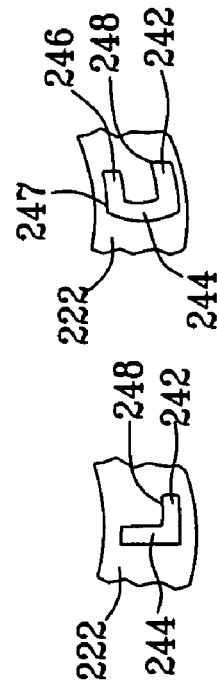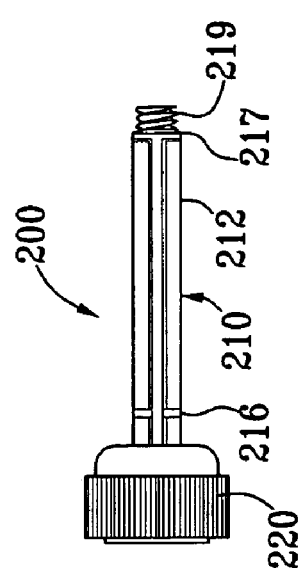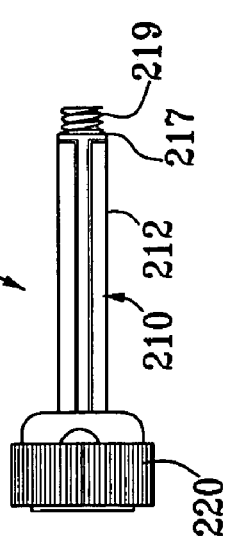

PASSIVE DELIVERY SYSTEM DILUENTS MIXING AND DELIVERY

FIELD OF THE INVENTION

This invention relates generally to syringe systems and methods for mixing and delivering a therapeutic agent formed by combining a diluent with a lyophilized drug or a concentrated drug. More specifically, this invention relates to syringe systems, including a passive needle guard, used for reconstitution of lyophilized or concentrated drugs and methods for using such systems.

BACKGROUND OF THE INVENTION

Lyophilization is a process by which the volatile components of a drug are removed in order to extend the shelf-life of the medication. Lyophilization may involve the rapid freezing of a material at a very low temperature followed by rapid dehydration. Solvents such as water are removed from the drug yielding a substance that is more stable and can be stored. Lyophilized drugs are generally stored in a glass vial or cartridge and covered by a rubber stopper or septum.

In order to administer the lyophilized drugs, the drug must generally be reconstituted. The reconstitution process usually involves adding a diluent such as sterile water to the lyophilized drug. A syringe is typically used to inject the diluent into the vial containing the lyophilized drug. The syringe may be pre-filled with the diluent or the user may first withdraw the diluent from a second vial or container into the syringe. After the diluent is added to the vial containing the lyophilized drugs, the contents are then mixed to form a therapeutic agent.

After complete mixing of the diluent and the lyophilized drug, the therapeutic agent may be aspirated back into the syringe. Generally, the same needle is used to withdraw the diluent into the vial and to aspirate the therapeutic agent into the syringe. In some systems, a separate, filtering needle is used to withdraw the therapeutic agent.

Once the therapeutic agent is in the syringe, the medication is administered to the patient. Usually the therapeutic agent is administered within a short time after reconstitution in order to ensure that the drug is not degraded by the solvent. The needle used during reconstitution is typically replaced with an administration needle. The administration needle usually will have a smaller diameter than the needle used during reconstitution to reduce tissue damage and pain to the patient during administration.

Most current systems for reconstitution expose the user to the risk of inadvertent needle sticks. In addition, current systems may not adequately prevent the possible reuse of the syringe. Because of these risks, a number of needle guards for syringes have been developed that are intended to prevent accidental needle sticks and/or inadvertent reuse of a syringe.

Accordingly, a syringe system that can be used for reconstitution and that would automatically activate a needle shield during or following administration of the therapeutic agent would be considered useful.

SUMMARY OF THE INVENTION

The present invention is directed to a syringe system for reconstitution of lyophilized or concentrated drugs. The present invention is also directed to the combination of such a system with a passive needle guard that is automatically activated to extend a shield to cover a needle of the syringe and to methods of making and using such systems. Typically, a passive needle guard shield is activated when a radial portion of a plunger contacts a lateral catch of the passive needle guard. As the radial portion of the plunger is moved distally, the lateral catch is forced laterally which results in a shield being forced distally to cover a needle of the syringe or in some designs, the syringe needle withdraws into the shield. A standard plunger and syringe cannot be used to reconstitute a lyophilized drug in conjunction with a passive needle guard because the plunger would activate the passive needle guard during reconstitution. The current system utilizes a longer plunger during reconstitution so that the passive needle guard is not activated during reconstitution. A radial element of the longer plunger does not contact the lateral catches of the passive needle guard when fully depressed distally. Thus, a user may reconstitute a lyophilized drug utilizing the longer plunger and then switch to a shorter, administration plunger to administer a therapeutic agent to a patient. Alternatively, a single plunger system may be used which can transition from an extended state to a shortened state. The extended state may be used during reconstitution. The user can then manually transition the plunger to the shortened state for administration of the lyophilized drug.

In accordance with one aspect of the present invention, a medicine cartridge, such as a syringe is provided. The syringe may be pre-filled with a diluent such as sterile water, or may be filled with the diluent at a later step. The syringe preferably includes a barrel having a distal end with a needle port and a proximal end configured to receive a plunger. A stopper may be inserted into the proximal end of the barrel. In a preferred embodiment, the proximal region of the stopper is configured to receive a plunger.

In a preferred embodiment, a passive needle guard is removably coupled with the syringe. The needle guard comprises a body, a shield, and a spring mechanism. The body comprises proximal and distal ends and a cavity therein for receiving the syringe. The distal end of the syringe may be inserted into the proximal end of the needle guard and then moved distally to couple the syringe with the needle guard. The proximal end of the body and the shield may comprise cooperating catches and one or more latch members. The cooperating catches hold the shield in a first, retracted position until the needle guard is activated.

A first, reconstitution plunger may be inserted by a user into the proximal end of the syringe or may be pre-attached. The reconstitution plunger comprises a radial element or thumb pad and a stem. The stem comprises a distal region that is configured to couple with a proximal region of the stopper. In a preferred embodiment, a length of the stem of the reconstitution plunger is substantially greater than a length of the barrel of the syringe to prevent the shield of the needle guard from moving distally to cover the needle.

A reconstitution needle may also be pre-attached to the needle port on the distal end of the syringe. The user may insert the reconstitution needle through a rubber stopper or other cap of a vial containing a lyophilized drug or concentrated drug. The user can then withdraw the diluent from the syringe and mix the diluent and lyophilized drug to form a therapeutic agent. Using the reconstitution needle, the user may then aspirate the therapeutic agent back into the syringe. Alternatively, the user may remove the reconstitution needle and insert a filtering needle into the needle port prior to aspiration of the therapeutic agent into the syringe.

The reconstitution plunger is then removed from the stopper and an administration plunger is coupled to the stopper. The administration plunger comprises a radial element or thumb pad and a stem. The stem comprises a distal region that is configured to couple with the stopper. A length of the stem of the administration needle is longer than the length of the barrel, but substantially shorter than the length of the stem of the reconstitution plunger. In another embodiment, a single plunger may be used which is able to transition from an extended, reconstitution state to a shortened, administration state.

Upon administration of the therapeutic agent via the syringe, the thumb pad of the plunger contacts one or more latch members which separate the cooperating catches of the shield and body. This results in the shield being biased by the spring mechanism distally. The shield is thereafter moved to the extended position by the spring, and covers the administration needle. The needle guard may include additional cooperating catches configured for engaging one another when the shield is disposed in the extended position to prevent retraction of the shield from the extended position.

BRIEF DESCRIPTION OF THE DRAWINGS

FIGS. 7A, 7B, 7C and 7D show an alternative embodiment of the present invention using a single plunger system.

FIGS. 7E and 7F are exploded views of a portion of a proximal cap of the single plunger system.

DESCRIPTION OF THE PREFERRED EMBODIMENTS

Figure 1:
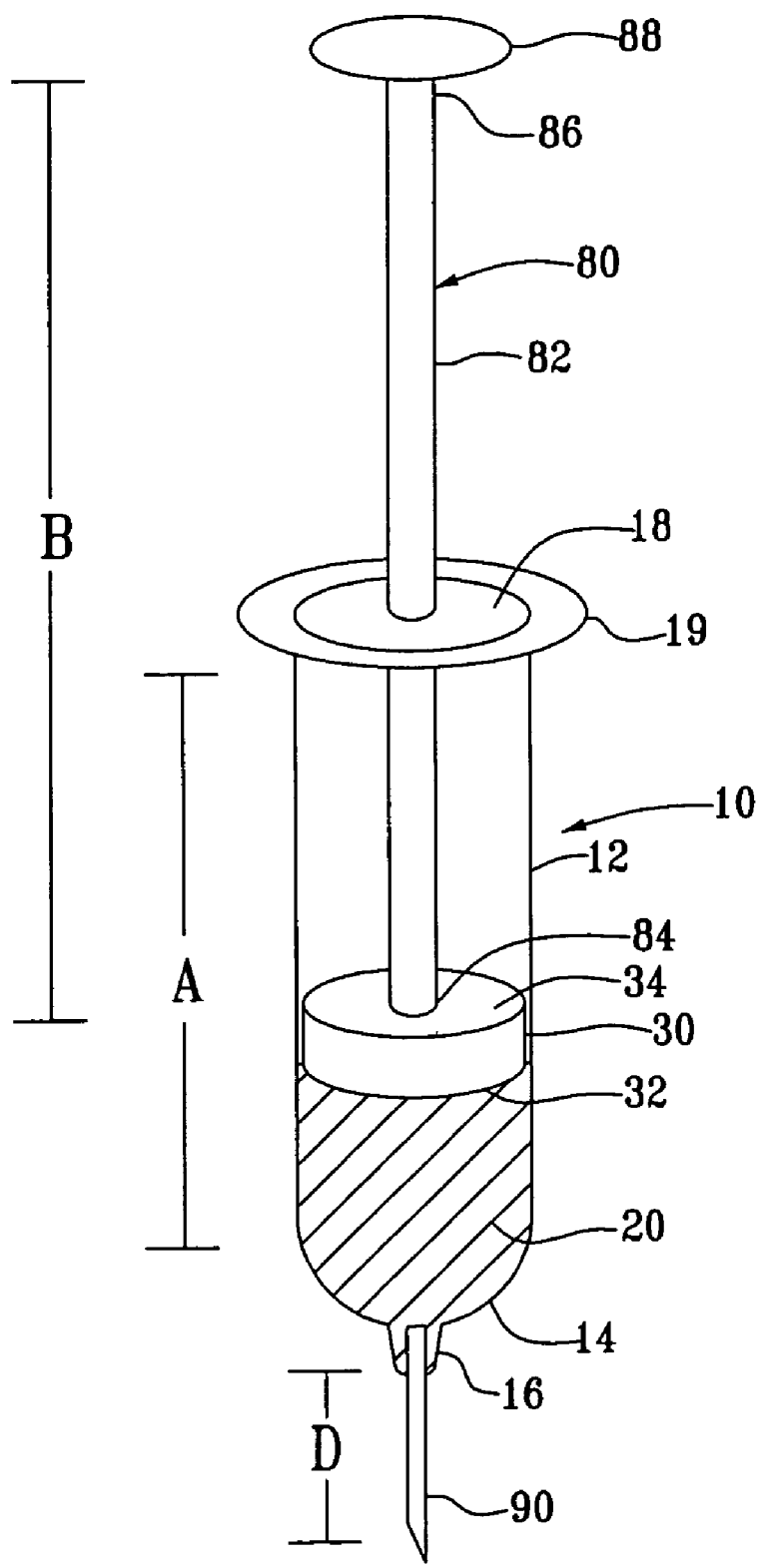
FIG. 1 shows a syringe system of the present invention as used during reconstitution in the preferred embodiment with a reconstitution plunger in a proximal position.

Turning to the drawings, FIG. 1 shows a preferred embodiment of a syringe used during reconstitution. Preferably, the syringe 10 has a substantially smooth-walled cylindrical barrel 12 having a length A, a distal end 14 or hub that is the administration end, and a proximal end 18 having a flange 19. The cylindrical barrel 12 typically is manufactured from substantially clear glass. Alternatively, the barrel 12 may be manufactured from plastic, e.g., polypropylene, k-resin, or polycarbonate, and the like. The proximal end 18 of the barrel 12 is configured to receive a stopper 30 and a plunger as discussed further below.

Figure 8:
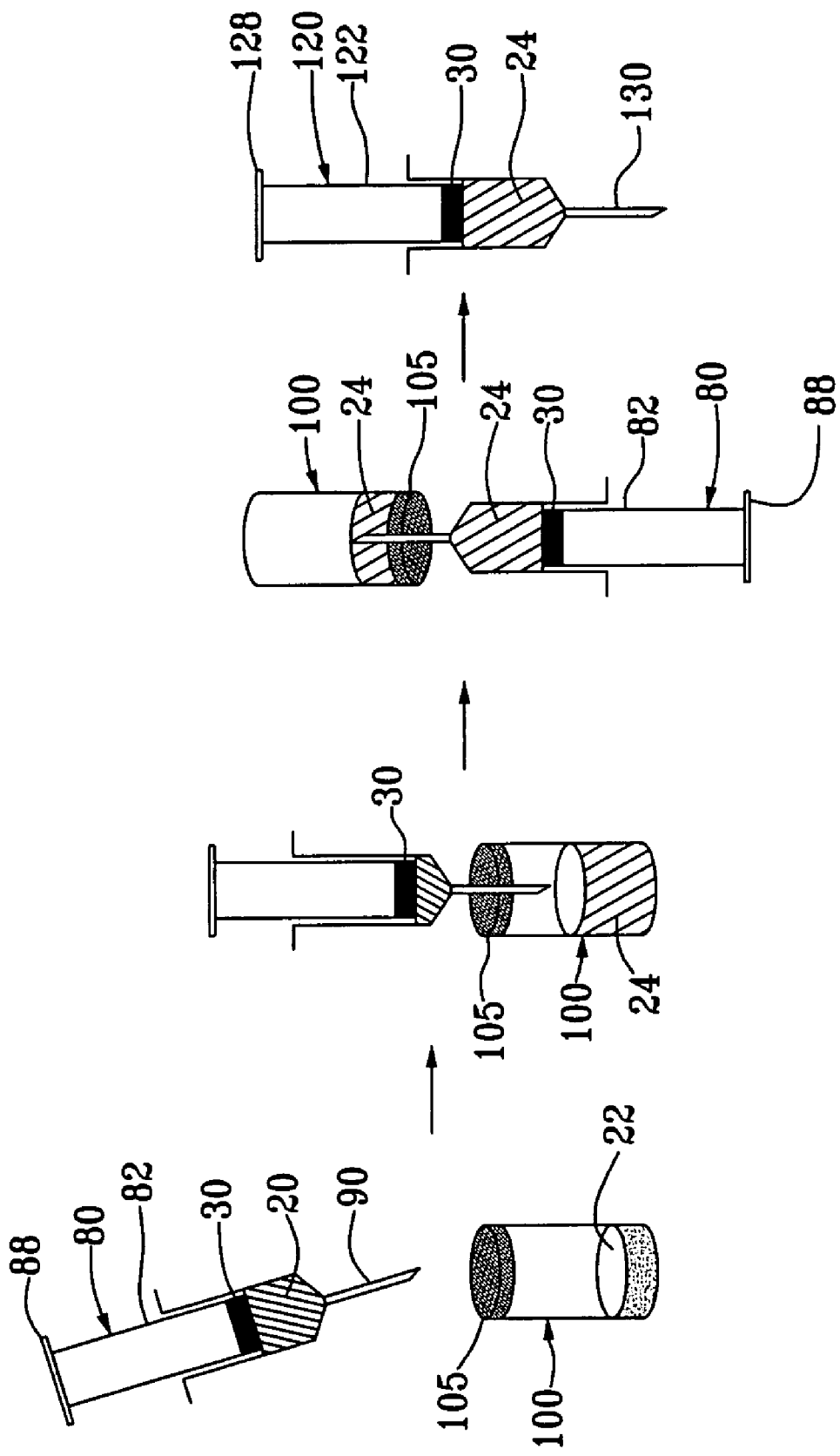
FIG. 8 is a flow diagram, showing a method of the present invention.

The distal end 14 of the cylindrical barrel 12 comprises a needle port 16. The needle port 16 is configured to removably couple a reconstitution needle 90. The needle port 16 may be configured to couple with several different sizes of needles with different diameters and lengths. The needles may be connected by a Luer connector, Luer slip, Luer, or other needle holder as is known in the art. The needle port 16 is configured to allow interchanging of the needle so a user (not shown) may use the most appropriate needle during filling the syringe 10, reconstitution, and administration of the medication to a patient (not shown). As is described further below, the user may use a larger reconstitution needle 90 during the process of filling the syringe 10 and reconstitution, but may then exchange the reconstitution needle 90 for a smaller administration needle 130 (FIGS. 3A-C, 5, 6, and 7) during administration of a therapeutic agent 24 to the patient. The reconstitution needle 90 may have a larger diameter than the administration needle 130 and may be used during filling and reconstitution to decrease the amount of time necessary for these steps. The higher gauge (smaller diameter) administration needle 130 may then be used to administer the therapeutic agent 24 to the patient in order to lower potential tissue damage or injury and reduce pain to the patient. Additionally, the reconstitution process may also act to dull or bend the reconstitution needle 90 because the reconstitution needle 90 is used to pierce a rubber stopper or seal 105 of a vial 100 containing the lyophilized drug 22 or medication to be diluted (FIG. 8). Therefore, in a preferred embodiment, the needle port 16 of the syringe 10 preferably allows the user to exchange the needle easily.

A stopper 30 is inserted into the cylindrical barrel 12 at the proximal end 18 (FIG. 1). The stopper 30 may be pre-attached to the syringe 10 or may be inserted by the user at a later step. The stopper 30 is configured to be slidably coupled into cylindrical barrel 12 and movable from a proximal position to a distal position. The stopper 30 is preferably made of pliable rubber, thermoplastic rubber, plastic, or similar material. The stopper 30 comprises a distal end 32 and a proximal end 34. The distal end 32 of the stopper is configured to create a seal against the cylindrical barrel 12 of the syringe 10. The proximal end 34 may include threaded layers (not shown). The threaded layers are configured to receive threaded portions (not shown) of a distal region of a stem of a plunger as discussed further below.

The syringe 10 may be pre-filled with a diluent 20. Preferably the syringe 10, if pre-filled, also comprises a label or markings (not shown) that indicate the quantity and type of diluent 20. For example, a sticker or label may be attached to the barrel 12 of the syringe 10 which provides the name of the diluent 20 and the volume of the diluent 20. The diluent 20 may be of any type known in the art including, but not limited to, sterile water and saline. Alternatively, the user may aspirate the diluent 20 into the syringe 10 from a vial or container 100 (FIG. 7) as discussed further below.

Figure 2:
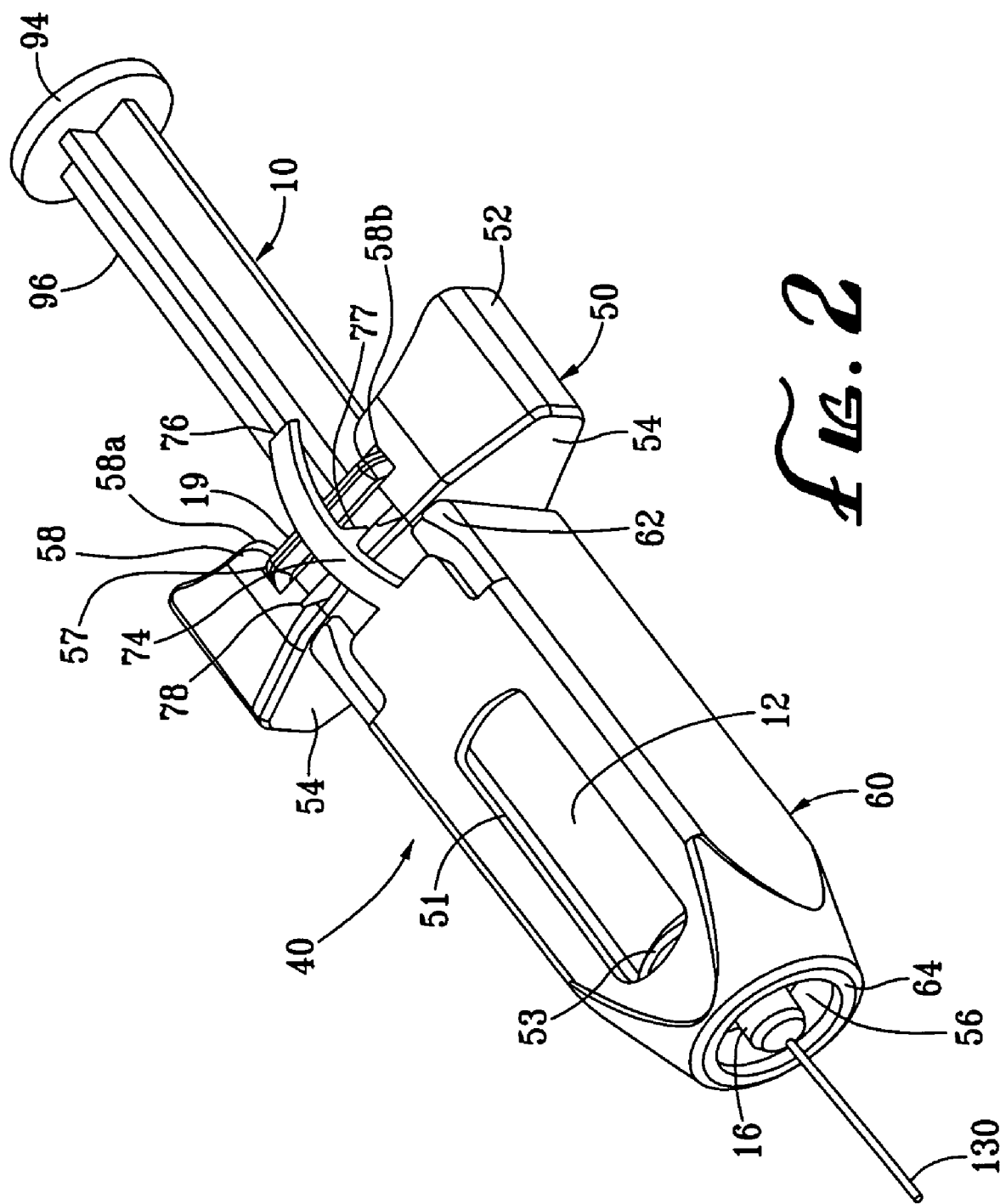
FIG. 2 is a perspective view of a preferred embodiment of the reconstitution syringe system of the present invention with a passive needle guard coupled to the syringe.
Figure 3:
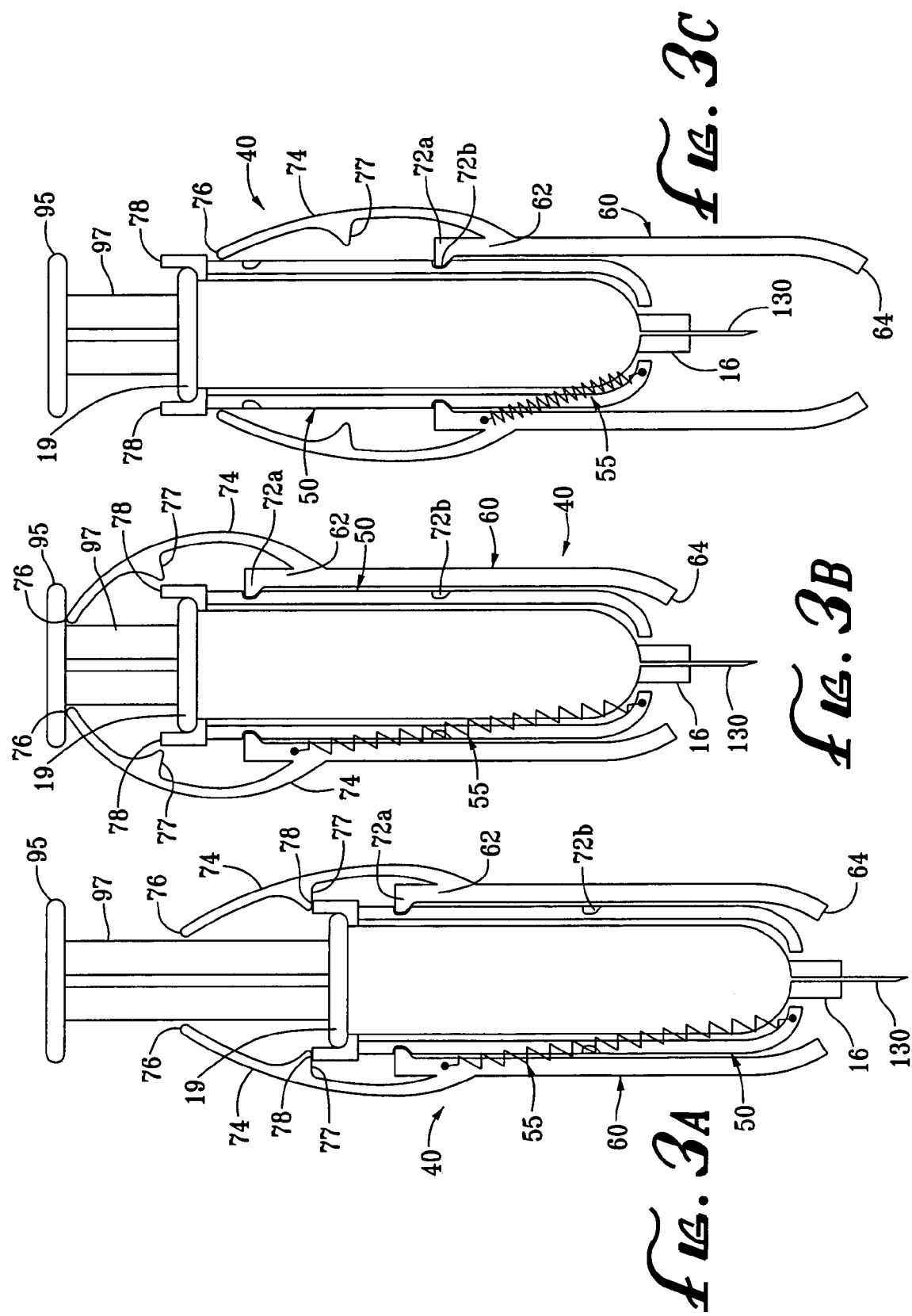
FIGS. 3A, 3B, and 3C are cross-sectional views of the passive needle guard of FIG. 2, showing activation of the shield as an administration plunger of the syringe is depressed.

Turning to FIG. 2, in a preferred embodiment, the syringe 10 is mounted in a needle guard 40. The needle guard 40 can be a passive needle guard system such as that disclosed in copending U.S. patent application Ser. No. 09/566,224, filed May 5, 2000, the disclosure of which is incorporated herein by reference. The passive needle guard 40 generally comprises a body 50 for receiving and holding the syringe 10, a shield 60 slidably attached to the body 50, and a spring mechanism 55 (FIGS. 3A-3C). Both the body 50 and the shield 60 are generally molded from plastic, such as, polypropylene, k-resin, or polycarbonate, or the like. In a preferred embodiment, the body 50 and the shield 60 are substantially clear to facilitate observation of the syringe 10 therein. Alternatively, the body 50 and the shield 60 may be translucent or opaque, and may be colored, such as a latex color, a flesh tone, or a primary color.

The body 50 may comprise opposing side rails defining two elongate openings or windows 51 extending at least partially between a proximal end 52 and a distal end 53 of the body 50. A substantially rigid collar (not shown) is molded on the distal end 53 of the body 50; the collar preferably has a substantially annular shape. The collar defines an opening 56 for allowing a needle on a syringe 10 received in the opening 56 to extend distally beyond the body 50.

The proximal end 52 of the body 50 preferably includes two finger grips 54 or protrusions on opposite sides of the body 50. The finger grips 54 may facilitate controlling the rate of the movement of the needle guard 40 relative to the syringe 10. Alternatively, the body 50 may include a single finger grip 54 that extends around the entire outer periphery or circumference of the proximal end 52 of the body 50.

The shield 60 is a tubular member adapted to slidably fit on the body 50 and has a proximal end 62 and a distal end 64. One or more latch members 74 extend proximally from the proximal end 52, 62 of one of the shield 60 and body 50. The latch member 74 may include a first catch 77 that is configured to engage a second catch 78 on the proximal end 52 of the body 50 of the needle guard 40. Engagement between the first catch 77 and the second catch 78 retain the shield 60 in a first, retracted position. Preferably, the one or more latch members 74 are elongate fingers having a proximal tip 76 that is engageable by a radial element 94 of a plunger 96 as it is depressed to axially compress and deflect the one or more latch members 74 radially outwardly, as is discussed further below.

The passive needle guard 40 also preferably includes a spring mechanism 55 (FIGS. 3A-3C) coupled to the body 50 and the shield 60 for biasing the shield 60 towards an extended position. The spring mechanism 55 may be a compression spring disposed between the body 50 and the shield 60, for example, disposed concentrically within the shield 60 adjacent to one end of the body 50 or within elongate passages defined by the shield 60 and/or body 50.

In addition, the passive needle guard 40 may include a locking mechanism on the proximal end 52 of the body 50, such as one or more locking detents 58 on a finger grip 54 thereof, for substantially securing the syringe 10 in the cavity (FIG. 2). The needle guard 40 is slidably mounted to the syringe 10. To assemble the syringe 10, the distal end 14 of the barrel 12 may be inserted into the proximal end 52 of the body 50 of the needle guard 40. The needle guard 40 may then be moved proximally such that the proximal end 52 of the needle guard 40 is coupled with the proximal end 18 of the syringe 10. The body 50 of the needle guard 40 and the proximal end 18 of the syringe 10 may be secured by the one or more locking detents 58 attached to the proximal end 52 of the body 50 of the needle guard 40. The locking detents 58 may have tapered proximal edges 58a, allowing the syringe 10 to be directed further distally, the flange 19 moving the locking detents 58 aside and entering the slot 57 (FIGS. 2 and 3A-3C). The locking detents 58 have substantially blunt distal edges 58b that prevent the syringe 10 from being removed proximally from the slot 57, thereby substantially permanently locking the syringe 10 into the body 50, and preventing axial (i.e. proximal and/or distal) movement of the syringe 10 within the passive needle guard 40 (FIG. 2).

As shown in FIGS. 3A-3C, the passive needle guard 40 also includes second cooperating 72a, 72b detents on the shield 60 and body 50 that are configured for engaging one another when the shield 60 is disposed in the extended position to prevent retraction of the shield 60 from the extended position.

In operation the shield 60 may be biased by the spring mechanism 55 from the first, or retracted, position wherein the needle 130 of the syringe 10 is exposed, towards the second, extended position wherein the shield 60 covers the needle 130 (FIGS. 3A-3C). One or more latch members 74 extend proximally from the shield 60 and are engageable by a radial element 95 of a plunger 97. The first catch 77 on the one or more latch members 74 and the second catch 78 on the body 50 of the needle guard 40 act to retain the shield 60 in the first, retracted position. As the plunger 97 is advanced distally within the syringe 10, the radial element or thumb pad 95 of the plunger 97 may contact the one or more latch members 74 and release the first catch 77 and second catch 78 whereupon the shield 60 may slide towards the second, extended position. The one or more latch members 74 may include a proximal tip 76 configured for engaging the radial element 95 of the plunger 97. Also, the needle guard 40 may comprise distal cooperating detents 72a, 72b that retain the shield 60 in the second, extended position. Therefore, once the shield 60 has been triggered to advance to the extended position, the administration plunger 120 and the shield 60 may be locked in a distal position thereby preventing reuse of the needle 130, reducing the risk of accidental needle sticks, and/or facilitating the disposal of the syringe 10.

Figure 4:
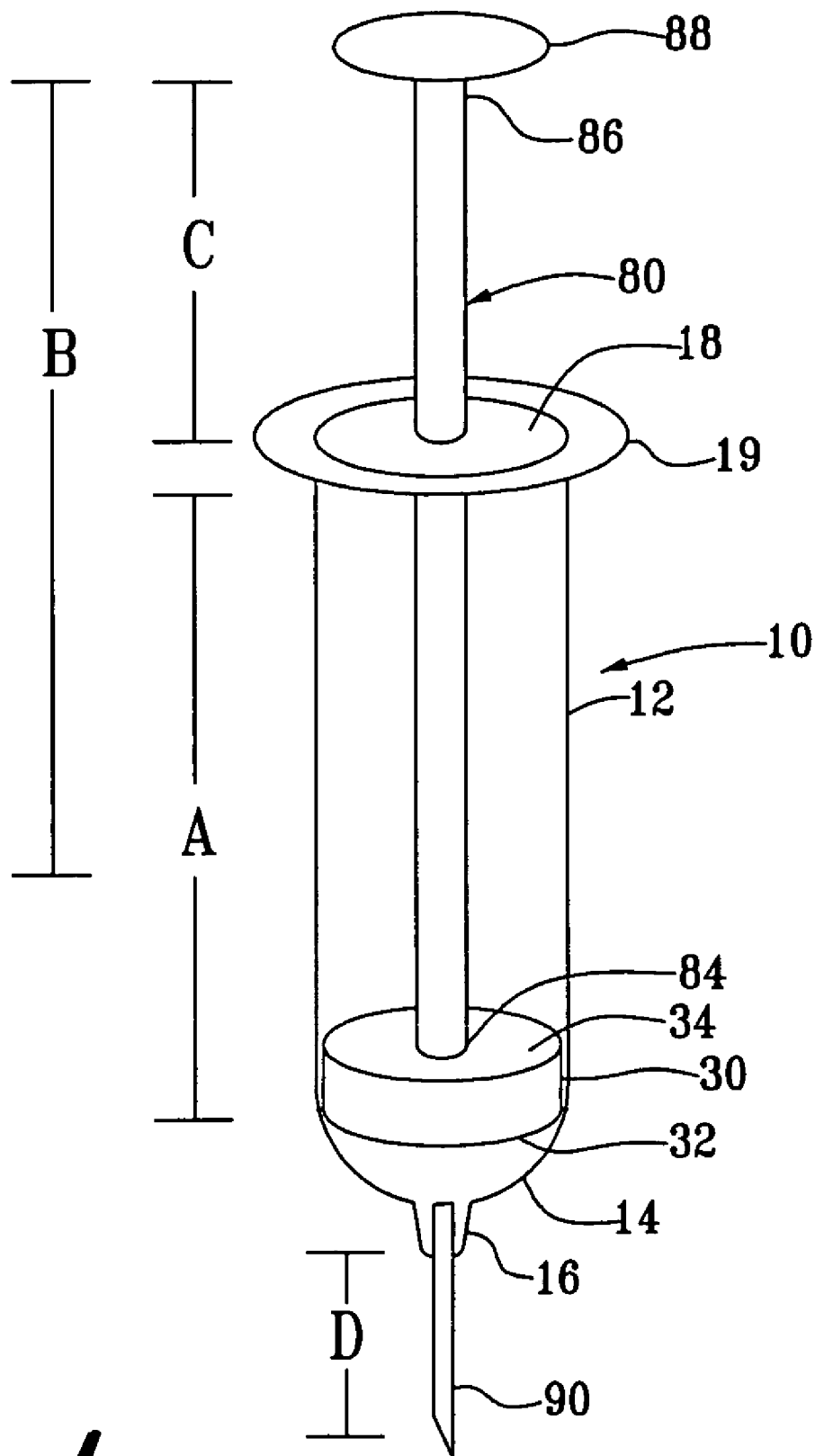
FIG. 4 shows the syringe system of FIG. 1 with the reconstitution plunger in a distal position.

The reconstitution system may utilize a two plunger system or a single plunger that is able to transition from an extended state to a shortened state. As shown in FIGS. 1 and 4, in the two plunger system, the syringe 10 includes a first plunger of a longer length as will be discussed further below. In a preferred embodiment, a first, reconstitution plunger 80 is pre-inserted into the proximal end 18 of the barrel 12 and is configured to be removably coupled with the stopper 30. Alternatively, the reconstitution plunger 80 can be inserted into the proximal end 18 of the barrel 12 and coupled with the stopper 30 in a separate step. The first plunger, or reconstitution plunger 80, comprises a stem 82 and a radial portion or thumb pad 88. The reconstitution plunger 80 may be made of plastic, e.g. polypropylene, k-resin, or polycarbonate, and the like.

The stem 82 has a length B, a distal region 84 and a proximal region 86. The distal region 84 of the stem 82 preferably comprises a threaded region (not shown). The threaded region is configured to couple with the threaded layers (not shown) of the proximal end 34 of the stopper 30. The user may insert the stem 82 into the proximal end 34 of the stopper 30 by rotating or screwing the reconstitution plunger 80 into the stopper 30. To disengage the reconstitution plunger 80 from the stopper 30, the user may rotate or unscrew the stem 82 of the reconstitution plunger 80 and move the reconstitution plunger 80 proximally away from the stopper 30.

The length B of the stem 82 of the reconstitution plunger 80 is greater than the length A of the cylindrical barrel 12 of the syringe 10. The length B of the stem 82 of the reconstitution plunger 80 is dimensioned to prevent the needle guard 40 from being activated via depression of the plunger during reconstitution. Therefore, upon complete depression of the reconstitution plunger 80, the needle guard 40 is not activated. As shown in FIG. 4, in a preferred embodiment the proximal region 86 of the stem 82 comprises a length C that represents the portion of the stem 82 that does not enter the cylindrical barrel 12 when the stem 82 is fully inserted into the cylindrical barrel 12. That-is, length C represents the portion of the stem 82 that protrudes from the cylindrical barrel 12 when the reconstitution plunger 80 is fully depressed in the distal direction.

Upon complete distal depression of the reconstitution plunger 80, the radial element 88 of the reconstitution plunger 80 does not contact the one or more latch members 74 of the needle guard 40. Therefore, even when the reconstitution plunger 80 is moved to its most distal position, the passive needle guard 40 is not activated and the shield 60 remains in the first, retracted position, and the needle 90 remains exposed.

In the preferred embodiment, a first, reconstitution needle 90 is provided. The reconstitution needle 90 may be pre-attached to the needle port 16, or may be attached by a user in a subsequent step. The reconstitution needle 90 may be comprised of stainless steel or other material known in the art. The reconstitution needle 90 may have a length D that is greater than a length of a standard hypodermic needle. In addition, the reconstitution needle 90 may have a -greater diameter than a standard hypodermic needle in order to reduce the time necessary for reconstitution. Preferably, the reconstitution needle 90 is not used to administer a therapeutic agent 24 to a patient. As discussed further below, the reconstitution needle 90 may be removed from the needle port 16 and replaced with an administration needle 130 after reconstitution has been completed and prior to administration of the therapeutic agent 24.

The reconstitution needle 90 may be removed prior to aspiration of the therapeutic agent 24 into the syringe 10. A filtering needle (not shown) may be inserted into the needle port 16 in order to aspirate the therapeutic agent. The filtering needle may ensure that portions of the lyophilized drug 22 that were not properly mixed are not administered to the patient.

Figure 5:
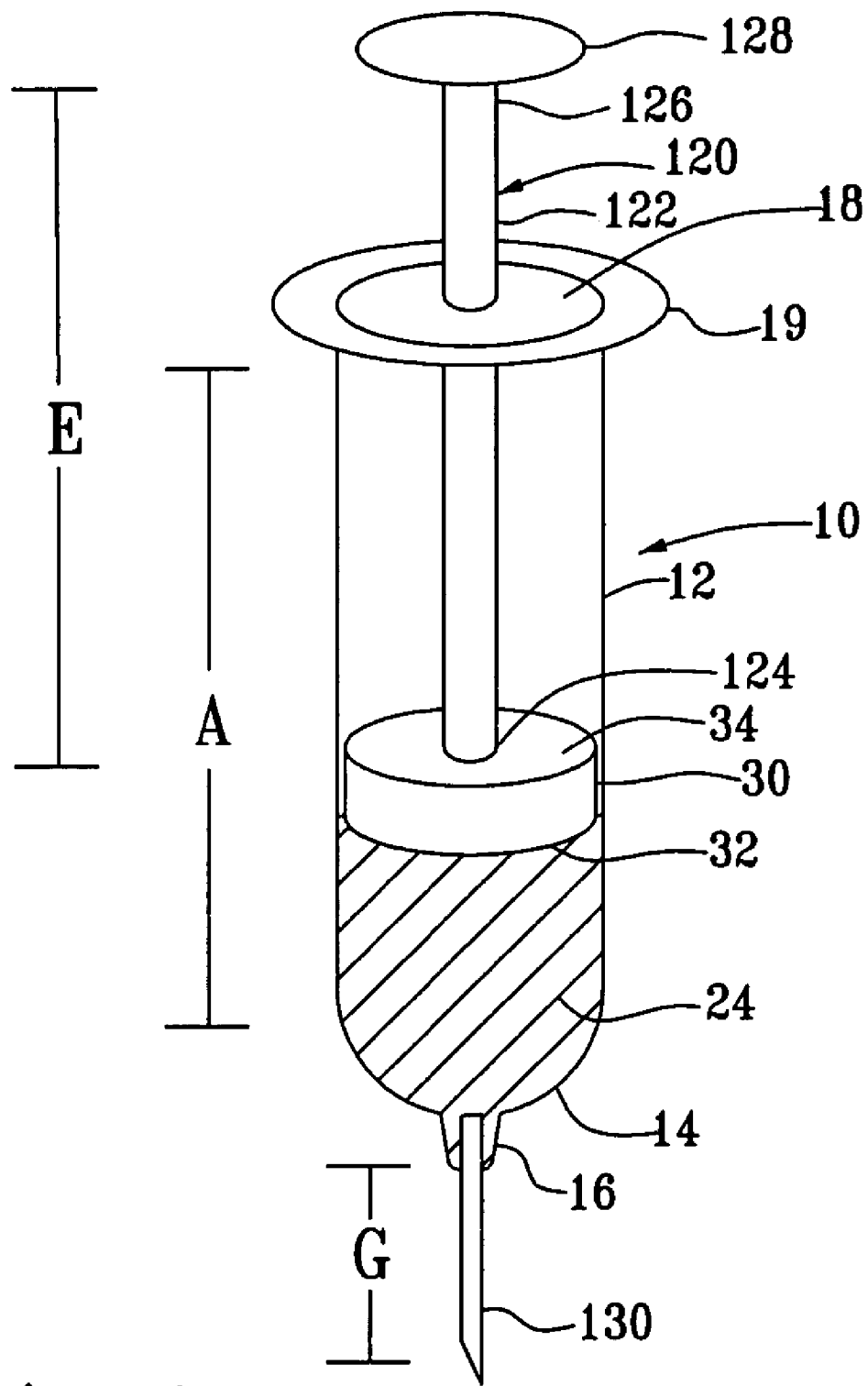
FIG. 5 shows the syringe system of the present invention as used during administration in the preferred embodiment with the administration plunger in a proximal position.
Figure 6:
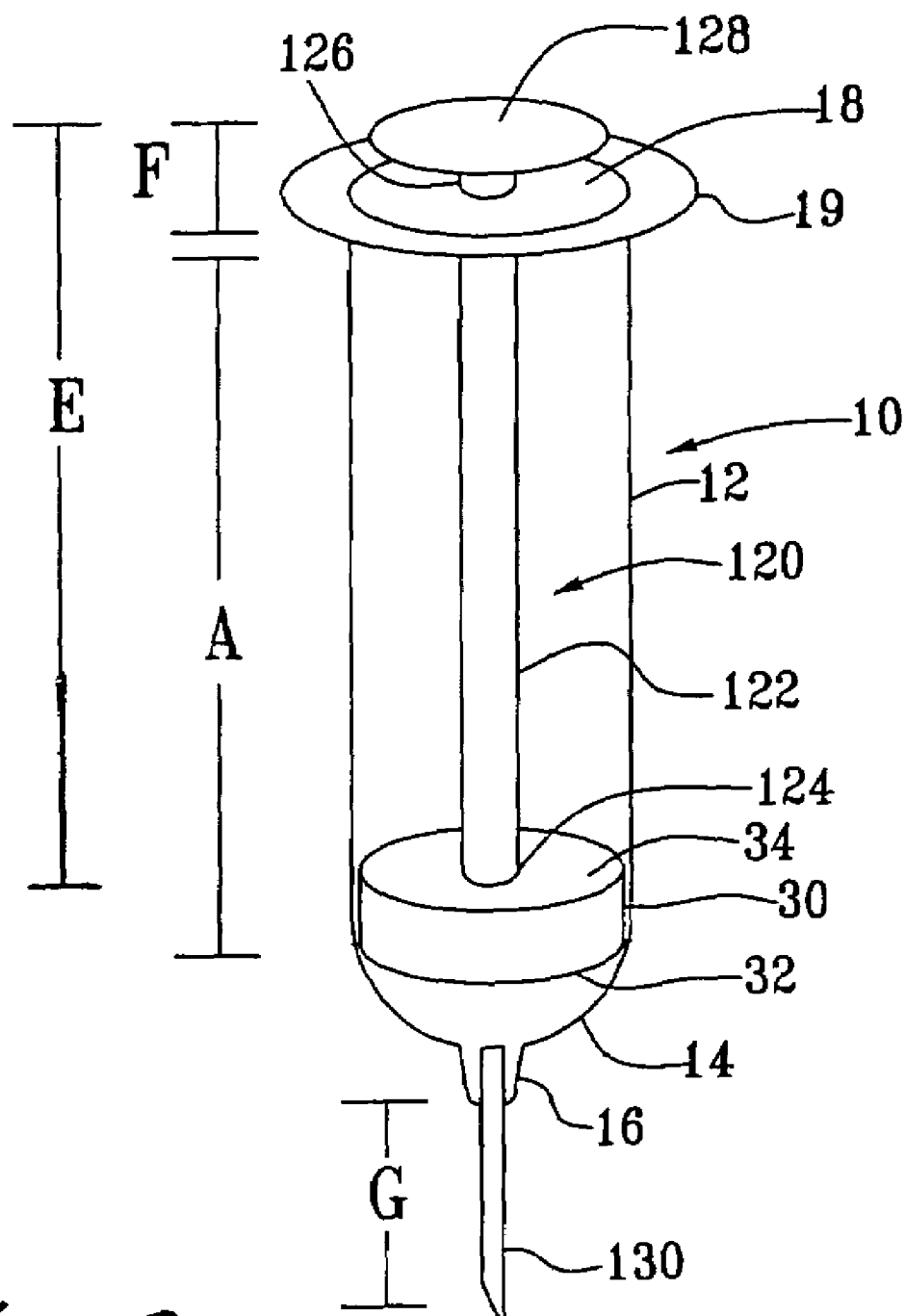
FIG. 6 shows the syringe system of FIG. 5 with the administration plunger in a distal position.

As shown in FIGS. 5 and 6, a second, administration plunger 120 which is shorter than the reconstitution plunger 80 may be used to administer the therapeutic agent to a patient. The administration plunger 120 comprises a stem 122 and a radial portion or thumb pad 128. The administration plunger 120 may be made of plastic, e.g. polypropylene, k-resin, or polycarbonate, and the like.

The stem 122 of the administration plunger 120 comprises a length E, a distal region 124 and a proximal region 126. The distal region 124 of the stem 122 preferably comprises a threaded region (not shown). The threaded region is configured to couple with the threaded layers (not shown) of the stopper 30. The user may insert the distal region 124 of the stem 122 into the stopper 30 by rotating or screwing the administration plunger 120 into the stopper 30.

The length E of the stem 122 of the administration plunger 120 is greater than the length A of the cylindrical barrel 12 of the syringe 10. However, unlike the stem 82 of the reconstitution plunger 80, the length E of the stem 122 of the administration plunger 120 is only slightly greater than the length A of the barrel 12 of the syringe 10. Therefore, the length E of the stem 122 of the administration plunger 120 is preferably shorter than the length B of the stem 82 of the reconstitution plunger 80. As shown in FIG. 6, the proximal region 126 of the stem 122 of the administration plunger 120 comprises a length F that represents the portion of the stem 122 that does not enter the cylindrical barrel 12 when the stem 122 is fully inserted into the cylindrical barrel 12. That is, length F represents the length of the portion of the stem 122 that extends out from the cylindrical barrel 12 when the administration plunger 120 is fully depressed in the distal direction. In a preferred embodiment, length F is less than length C.

In a single plunger system, the plunger 200 may be configured to transition from an extended, reconstitution position (FIG. 7A) to a shortened, administration position (FIG. 7B). Preferably, the single plunger system comprises a stem portion 210, a proximal cap 220, and a spring 230 (FIG. 7C). The stem portion 210 of the single plunger 200 comprises a stem 212, a radial element 214 disposed on the proximal end 215 of the stem 212, and a tab 216 (FIG. 7A) disposed near the proximal end 215 of the stem 212. Preferably, the radial element 214 comprises one or more lateral tabs 218 which are configured to communicate with channels 242, 244, 246 located on the proximal cap 220 as discussed further below (FIGS. 7C, 7E, 7F). In a preferred embodiment, the distal end 217 of the stem 212 further comprises a threaded region 219 designed to engage threaded layers of a stopper (not shown).

The proximal cap 220 is configured to engage the stem 212 and cover the radial element 214. The proximal cap 220 includes a body 222 and a head 224. The body 222 is configured to slidably engage the stem 212 of the plunger 200 and is disposed between the proximal end 215 of the stem 212 and the tab 216 disposed on the stem 212. The distal end 223 of the body 222 is designed such that the body 222 can only move between the radial element 214 and the tab 216. The body 222 of the proximal cap 220 comprises one or more grooves or channels 242, 244, 246 configured to retain the one or more lateral tabs 218 disposed on the radial element 214 of the stem 212. The grooves or channels 242, 244, 246 include a main vertical channel 244 and a distal horizontal channel 242 (FIG. 7E). In a further embodiment, the body 222 may include a second horizontal channel 246 disposed at the proximal end 247 of the vertical channel 244 (FIG. 7F). The body 222 is adapted to engage the head 224 of the proximal cap 220. The head 224 and body 222 may be joined together by any means known in the art such as an adhesive, complementary grooves or tabs, or the like. The spring 230 is preferably disposed between the radial element 214 of the stem 212 and the distal portion 223 of the body 222 of the proximal cap 220. The spring 230 may be of any type known in the art. The spring 230 provides a force on the proximal cap 220 forcing the proximal cap 220 distally.

In operation, the single plunger system is initially in an extended, reconstitution state (FIG. 7A). In this state, the lateral tab 218 attached to the radial element 214 is disposed in the distal horizontal channel 242 of the body 222 of the proximal cap 220. The distal force exerted by the compressed spring 230 forces the lateral tab 218 against a proximal wall 248 of the horizontal channel 242 thereby effectively locking the plunger 200 in the extended state. After the user has completed the necessary steps to reconstitute the drugs as discussed further below, the user twists the proximal cap 220. Twisting of the proximal cap 220 acts to move the lateral tab 218 in relation to the horizontal channel 242. This allows the lateral tab 218 to enter the vertical channel 244 and the force of the compressed spring 230 moves the lateral tab 218 to the proximal end 247 of the vertical channel 244. During administration of the lyophilized drug, the force of the spring 230 combined with the distal force exerted by the user during administration keeps the plunger 200 in the shortened, administration state (FIG. 7B). If the body 222 comprises a proximal horizontal channel 246, the proximal cap 220 can be twisted to position the lateral tab 218 within the proximal horizontal channel 246 which would further "lock" the lateral tab 218 in the proximal position during administration of the drug.

As shown in FIGS. 5 and 6, in a preferred embodiment, an administration needle 130 is coupled with the needle port 16 prior to administration of the therapeutic agent 24 to the patient. The administration needle 130 may be stainless steel or other material as known in the art. The administration needle 130 can be of any length G and gauge known in the art. Preferably, the length G and diameter of the administration needle 130 is selected based on the needs of the patient. The length G of the administration needle 130 may depend on several factors including the type of injection to be given (e.g., intramuscular, subcutaneous, or intradermal), the size of the patient, and the site of injection. The gauge of the administration needle 130 should be selected based on the needs of the patient as well as the viscosity of the therapeutic agent 24. In a preferred embodiment, the gauge of the administration needle 130 is higher (i.e. a smaller needle diameter) than the gauge of the reconstitution needle 90.

Returning to FIGS. 3A-3C, a passive needle guard 40 is attached to the syringe 10, and the radial element or thumb pad 95 of the plunger 97 is configured to engage the one or more latch members 74 of the needle guard 40. Therefore, when the user fully depresses the plunger 97 in the distal direction, the radial portion 95 of the plunger 97 engages the one or more latch members 74 of the needle guard 40. The radial portion 95 of the plunger 97 forces the one or more latch members 74 laterally. As discussed above, this lateral movement of the one or more latch members 74 allows the first catch 77 and second catch 78 to disengage and the shield 60 is then forced distally and to cover the administration needle 130.

In the two plunger system, the full distal depression of the administration plunger 120 activates the passive needle guard 40. As discussed above, this is in contrast to a similar distal depression of the longer reconstitution plunger 80. Therefore, in order to utilize the passive needle guard 40, it is necessary that the user replace the reconstitution plunger 80 with the administration plunger 120. In a single plunger system, the passive needle guard 40 is not activated by the full distal depression of the plunger 200 when the plunger 200 is in the extended, reconstitution state (FIG. 7A). However, once a user has transitioned the plunger 200 to the shortened, administration state (FIG. 7B), the full distal depression of the plunger 200 would activate the passive needle guard 40.

The syringe 10 can be used to administer a lyophilized or concentrated drug 22 to a patient. The lyophilized drug or concentrated drug 22 may be of any type known to those of skill in the art. Preferably, the lyophilized or concentrated drug 22 is stored in a vial or container 100 such as a glass vial (FIG. 8). The vial 100 may include a cover such as a rubber stopper or cap 105 that can be penetrated by a needle. In a preferred embodiment, the vial 100 is made of a substantially clear glass so that the user can ensure that the diluent 20 and lyophilized drug 22 have been properly and fully mixed.

As schematically shown in FIG. 8, in a two plunger system, the syringe 10 has a reconstitution plunger 80 and/or a stopper 30 pre-attached. The reconstitution plunger 80 and stopper 30 may be inserted into a proximal end 18 of a cylindrical barrel 12 of the syringe 10. Alternatively, the user may couple the reconstitution plunger 80 to the stopper 30 by twisting or screwing a distal region 84 of a stem 82 of the reconstitution plunger 80 into threaded layers (not shown) of a proximal end 34 of the stopper 30. The reconstitution plunger 80 and/or stopper 30 can then be inserted into a proximal end 18 of the syringe 10.

Preferably, a reconstitution needle 90 is pre-attached to a needle port 16 on a distal end 14 of the cylindrical barrel 12 of the syringe 10 via a Luer, Luer lock, Luer slip, or other method as known in the art. If the reconstitution needle 90 is not pre-attached, the user may couple the reconstitution needle 90 to the needle port 14. In addition, a passive needle guard 40 (FIG. 2) may be attached to the syringe 10 as discussed above.

The syringe 10 may be pre-filled with a diluent 20 such as sterile water, saline or other solvent. Alternatively, the diluent 20 may be stored in a container such as a vial 100 (FIG. 8). The user may aspirate the diluent 20 from the vial into the barrel 12 of the syringe 10 by inserting the reconstitution needle 90 into the vial containing the diluent 20 and moving the reconstitution plunger 80 proximally.

Once the diluent 20 is in the syringe 10, the user can reconstitute the lyophilized or concentrated drug 22. Typically, the user will sterilize the rubber stopper 105 by wiping it with alcohol or other method known in the art. Then the user may insert the reconstitution needle 90 into the rubber stopper 105 of the vial 100. Insertion of the reconstitution needle 90 into the vial 100 may draw the diluent 20 into the vial 100 without requiring manipulation of the reconstitution plunger 80 by the user. However, to ensure that the diluent 20 has been completely withdrawn from the syringe 10, the user can distally depress a radial element or thumb pad 88 on the reconstitution plunger 80 to fully displace the diluent 20 from the syringe 10 and into the vial 100. The vial 100 comprising the diluent 20 and drug 22 can then be rotated or moved as appropriate in order to mix the diluent 20 and the drug 22 and form a therapeutic agent 24. Once the user has verified that the diluent 20 and drug 22 have been properly mixed, the user will then aspirate the therapeutic agent 24 back into the syringe 10 by placing the distal tip 92 of the reconstitution needle 90 into contact with the therapeutic agent 24 and moving the reconstitution plunger 80 proximally. The user may also invert the vial 100 during aspiration. In an alternative embodiment, the user may replace the reconstitution needle 90 with a filtering needle (not shown) before aspiration of the therapeutic agent 24 into the syringe 10. Once the desired amount of therapeutic agent 24 has been aspirated into the barrel 12 of the syringe 10, the user may then prepare the syringe 10 for administration of the therapeutic agent 24.

The reconstitution plunger 80 is removed by twisting or unscrewing the stem 82 of the reconstitution plunger 80 from the stopper 30. Next, an administration plunger 120 may be inserted. The administration plunger 120 comprises a radial element or thumb pad 128 and a stem 122 with a distal region 124 that is configured to couple with the stopper 30. The administration plunger 120 should be screwed into the stopper 30 without displacing the stopper 30 distally to ensure that the therapeutic agent 24 is not inadvertently withdrawn from the syringe 10. An administration needle 130 may be inserted into the needle port 16 after the user has removed the reconstitution needle 90 or filtering needle from the needle port 16. The reconstitution needle 90 or filtering needle may be removed from the needle port 16 by any method known in the art including unscrewing the reconstitution needle 90 or filtering needle from the needle port 16. The administration needle 130 can then be inserted and removably coupled with the needle port 16. Alternatively, the reconstitution needle 130 may be used to administer the therapeutic agent 24 to the patient.

The administration needle 130 is positioned as appropriate in order to administer the therapeutic agent 24 to the patient. Generally, the therapeutic agent 24 must be administered to the patient shortly after reconstitution. The user applies a distal force on the thumb pad 128 of the administration plunger 120 to inject the therapeutic agent 24 into the patient. If a passive needle guard 40 is attached, the shield 60 may also include a set of finger grips 54 on opposite walls of the shield 60 (FIG. 2). When present, the finger grips 54 may be grasped during the operation of the syringe 10 in order to control the speed of advancement of the shield 60 with respect to the syringe 10. The distal force is applied until the radial element 128 of the administration plunger 120 contacts the one or more latch members 74 of the needle guard 40. The user then further depresses the administration plunger 120 to radially deflect the one or more latch members 74 from the proximal end 18 of the syringe 10, whereupon the shield 60 is released from the first, retracted, position. After delivery of the therapeutic agent 24, the user withdraws the administration needle 130 from the patient's skin, and releases the administration plunger 120, whereby the shield 60 continues to advance distally with respect to the syringe 10 until the administration needle 130 is substantially contained within the shield 60. When the administration needle 130 is substantially contained within the shield 60, cooperating detents 72a, 72b on the shield 60 and on the body 50 of the needle guard 40 may engage one another to prevent subsequent movement of the syringe 10 with respect to the shield. The syringe 10 may then be disposed of using methods known in the art.

Operation of the single plunger system is completed in a similar fashion, except that only a single plunger 200 is used. The plunger 200 initially is positioned in an extended, reconstitution position (FIG. 7A) as discussed further above. Once the user has completed the reconstitution process, the user twists the proximal cap 220 of the single plunger system. This action transitions the plunger 200 from the extended state to the shorter, administration state (FIG. 7B). The user can then administer the reconstituted drug to the patient and the proximal cap 220 of the shortened plunger 200 will contact and activate the passive needle guard 40.

While the invention is susceptible to various modifications, and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

What is claimed:

1. A method of administering lyophilized drugs, the method comprising
    providing a syringe barrel including a proximal end being configured to receive a plunger and a stopper, a distal end, and a stopper coupled with the syringe barrel;
    inserting a reconstitution plunger into the proximal end of the syringe barrel, the reconstitution plunger being configured to be removably coupled with the stopper;
    aspirating a diluent from a diluent vial;
    displacing the diluent into a medication vial comprising a medication;
    mixing the diluent and the medication in the medication vial to form a therapeutic agent;
    withdrawing the therapeutic agent from the medication vial; and
    replacing the reconstitution plunger with an administration plunger comprising a radial element and being configured to be coupled with the stopper, wherein the administration plunger has a length smaller than a length of the reconstitution plunger.

2. The method of claim 1, further comprising removably coupling a reconstitution needle to the distal end of the syringe barrel.

3. The method of claim 2, further comprising replacing the reconstitution needle with an administration needle being configured to be removably coupled with the distal end.

4. The method of claim 1, further comprising administering the therapeutic agent to a patient.

5. The method of claim 1, further comprising coupling a needle guard to the injection device, the needle guard comprising a body and a shield.

6. The method of claim 5, further comprising displacing the shield of the needle guard in a distal direction by interacting a radial element of the administration plunger to activate the needle guard to cover the needle.

7. The method of claim 6, wherein one or more latch members are coupled with the body or shield of the needle guard and are releasable when the radial element interacts with the latch members.

8. The method of claim 1, wherein a length of the stem of the reconstitution plunger is greater than a length of the stem of the administration plunger.

9. The method of claim 1, wherein the diluent is water or saline.

10. The method of claim 1, wherein the medication is a lyophilized drug.

11. A method of administering lyophilized drugs, the method comprising
    providing an injection device pre-filled with a diluent, the injection device comprising a needle guard having a body and a shield, a syringe barrel including proximal and distal ends, a stopper coupled with the syringe barrel, a reconstitution plunger including a stem and being configured to be removably coupled with the stopper, and a reconstitution needle being configured to be removably coupled with the distal end;
    injecting the diluent into a medication vial comprising a medication;
    mixing the diluent and the medication in the medication vial to form a therapeutic agent;
    withdrawing the therapeutic agent from the medication vial;
    replacing the reconstitution needle with an administration needle; and
    replacing the reconstitution plunger with an administration plunger, the administration plunger comprising a stem and a radial element, wherein a length of the stem of the reconstitution plunger is greater than a length of the stem of the administration plunger.

12. The method of claim 11, wherein the needle guard further comprises a spring mechanism coupled to the body and the shield for biasing the shield distally towards the extended position.

13. The method of claim 11, further comprising displacing the shield of the needle guard in a distal direction by interacting a radial element of the administration plunger to activate the needle guard to cover the needle.

14. The method of claim 13, wherein one or more latch members are coupled with the body or shield of the needle guard and are releasable when the radial element interacts with the latch members.

15. The method of claim 11, wherein a length of the stem of the reconstitution plunger is greater than a length of the stem of the administration plunger.

16. A method of administering lyophilized drugs, the method comprising
    providing a syringe barrel including a proximal end being configured to receive a plunger and a stopper, a distal end, and a stopper coupled with the syringe barre;

inserting a plunger into the proximal end of the syringe barrel, the plunger being configured to be removably coupled with the stopper and being configured to transition from an extended, reconstitution length to a shortened, administration length;
aspirating a diluent from a diluent vial;
displacing the diluent into a medication vial comprising a medication;
mixing the diluent and the medication in the medication vial to form a therapeutic agent;
withdrawing the therapeutic agent from the medication vial; and
transitioning the plunger from the extended position to the shortened position.

17. The method of claim 16, further comprising administering the therapeutic agent to a patient.

18. The method of claim 16, further comprising coupling a needle guard to the injection device, the needle guard comprising a body and a shield.

19. The method of claim 18, further comprising displacing the shield of the needle guard in a distal direction by interacting a radial element of the plunger to activate the needle guard to cover the needle.

* * * * *